United States Patent
Berardesca

(10) Patent No.: US 7,780,995 B1
(45) Date of Patent: Aug. 24, 2010

(54) COMPOSITION BASED ON NATURAL EXTRACTS USEFUL IN THE PREVENTION AND TREATMENT OF CUTANEOUS WRINKLES

(75) Inventor: Enzo Berardesca, Pavia (IT)

(73) Assignee: Ceteris Holding B.V. - Amsterdam (Olanda) - Succursale di Lugano, Lugano (CH)

( * ) Notice: Subject to any disclaimer, the term of this patent is extended or adjusted under 35 U.S.C. 154(b) by 1193 days.

(21) Appl. No.: 10/257,869

(22) PCT Filed: Oct. 12, 2000

(86) PCT No.: PCT/EP00/10276

§ 371 (c)(1), (2), (4) Date: Apr. 23, 2003

(87) PCT Pub. No.: WO01/78674

PCT Pub. Date: Oct. 25, 2001

(30) Foreign Application Priority Data

Apr. 18, 2000 (CH) ........................ 776/00

(51) Int. Cl.
A61K 8/02 (2006.01)
A61K 35/12 (2006.01)
A61K 35/34 (2006.01)
A61K 36/00 (2006.01)
A61Q 11/00 (2006.01)

(52) U.S. Cl. .................. 424/725; 424/58; 424/401; 424/520; 424/548

(58) Field of Classification Search ............ None
See application file for complete search history.

(56) References Cited

U.S. PATENT DOCUMENTS

| 4,451,397 | A | * | 5/1984 | Huc et al. ............... 530/356 |
| 5,364,845 | A | * | 11/1994 | Henderson ............... 514/54 |
| 6,028,118 | A | * | 2/2000 | Dupont et al. .......... 424/548 |
| 6,147,054 | A | * | 11/2000 | De Paoli Ambrosi ...... 514/23 |
| 6,149,933 | A | * | 11/2000 | Nelson .................. 424/441 |
| 6,280,777 | B1 | * | 8/2001 | Bombardelli et al. ..... 424/756 |
| 6,347,986 | B1 | * | 2/2002 | Fujii ..................... 452/135 |
| 6,562,794 | B1 | * | 5/2003 | Lanzendorfer et al. .... 514/28 |
| 6,579,543 | B1 | * | 6/2003 | McClung ................ 424/728 |
| 6,756,065 | B1 | * | 6/2004 | Merizzi ................. 424/752 |

FOREIGN PATENT DOCUMENTS

| FR | 1433383 | | 1/1965 |
| FR | 2770976 | * | 5/1999 |
| WO | WO9623512 | | 8/1996 |
| WO | WO9833494 | | 8/1998 |
| WO | WO0178674 | | 10/2001 |

OTHER PUBLICATIONS

Database Prompt Online! STN International; AN 1999:21826, 1999; Simpson, Liz: *Supplementary Benefits and Beauty Counter*; ISSN: 0960-3751, Dec. 1998, p. 12; (XP-002165003).
BE 904 014 A Schifano Carmelo, May 2, 1986, p. 3, line 11-line 26.

* cited by examiner

*Primary Examiner*—David M. Naff
*Assistant Examiner*—Debbie K Ware
(74) *Attorney, Agent, or Firm*—Roylance, Abrams, Berdo & Goodman, L.L.P.

(57) ABSTRACT

A composition based on natural extracts useful in the prevention and treatment of cutaneous ageing and particularly wrinkles, which comprises in combination: leucocyanadines in the form of extract of *Vitis vinifera*; triterpenes in the form of an extract of *Centella asiatica*; fish cartilage extract.

26 Claims, No Drawings

COMPOSITION BASED ON NATURAL EXTRACTS USEFUL IN THE PREVENTION AND TREATMENT OF CUTANEOUS WRINKLES

The present invention relates to a composition based on natural extracts, intended for oral administration, for the therapeutic and/or cosmetic treatment of skin ageing phenomena, and in particular wrinkles.

Among the main objectives of modern dermatology is, without doubt, the etiopathogenetic understanding of that cutaneous phenomenon generally indicated with the term wrinkle.

Wrinkles—like cellulite and alopecia—are among the most unwelcome of unsightly characteristics, and are considered as the most characteristic indication of the transition from youth to old age.

From a pathogenetic point of view it is considered that the causes responsible for the formation of wrinkles may be:

1) chronological cutaneous ageing generally, in large part supported by the action of free radicals of oxygen;

2) degradation of the elastic fibres and alteration of collagen fibres by phenomena principally induced by the action of the metallo-protease released by keratinocites and fibroblasts in response to exposure to light;

3) muscular and articular movements; and 4) the force of gravity.

These four elements act in different amounts in the formation of wrinkles, giving rise to different types.

Currently wrinkles are classified thus:
network or fine mesh lines;
expression or muscle-following lines;
articulation lines;
muscular-cutaneous relaxation folds; and
position folds.

Of these the only wrinkles which can respond to treatment (peeling and surgery apart) are the cutaneous network lines and expression lines. These latter, in fact, already well defined by about twenty to thirty years, can become very deep and then become rather evident in subjects with chronic photo damage, independently of age. In this case, the expression lines become more marked because of the worsening relationship of the thicker and more rigid corneal layer, and of the thinner epidermis.

Consequently, rehydrating the skin, protecting it from ultra violet rays and—above all—stimulation with suitable substances, can obtain a partial reduction in the depth of the expression lines. Even better results can be obtained in the treatment of cutaneous network lines: these latter become ever more evident with the passage of the years and exposure to light and can appear and become very evident even starting from thirty to forty years.

The prevention of the said cutaneous ageing phenomena has been up to now based essentially on the use of high protection solar filters.

There are also known compositions for topical use, which use as active agents, retinoid and/or α-hydroxy acid derivatives.

The present invention provides an active, systemic, composition capable of preventing the formation of new wrinkles (particularly of network and expression lines) and to reduce and resist the aggravation of those already existing.

The invention also provide a composition useful for the treatment of skin stretch marks and skin relaxations.

It constitutes therefore an object of the invention to provide a composition based on natural extracts, useful in the above-mentioned treatments, characterised in that it comprises, in combination:

leucocyanidines in the form of an extract of *Vitis vinifera*;
triterpenes in the form of an extract of *Centella asiatica*; and
fish cartilage extract.

In particular, the extract of leucocianidine or leucoanthocianine of *Vitis vinifera* comprises procianidolic oligomers, typically dimers, trimers, tetramers, pentamers and heptamers, derived from the condensation of monomeric units of flavan-3-ols and flavan-3, 4-diolsfree or esterified or gallic acid.

Typically, the commercial extracts of leucocianidine are categorised in terms of their content of catechine and epicatechine which constitute the principal components thereof.

The principal active components in the commercial extracts have good bioavailability when orally administered; within the scope of the invention dry extracts can therefore be utilised as such. However, the use of phytosomal forms is preferable, which further improves the bioavailability of the active principle. In this form, leucocyanidines are complexed with phospholipids, particularly with soya distearoylphosphatidylcholine.

The triterpene fraction of *Centella asiatica* is obtained by extraction and purification of the aerial part of the *Centella asiatica*, also known as asiatic Hydrocotyl. Typically, this triterpene fraction comprises a mixture of madecassic acid (about 30% wt) asiatic acid (about 30% wt) and asiaticoside (about 40% wt).

These substances, with well known toxicological profile, recognise the fibroblast as principle target and perform their functions by interacting with it. It has been shown that these triterpenes accelerate the uptake and metabolism of lysine and proline, the two fundamental amino acids in the final structure of collagen and increase the synthesis and release of tropocollagens, likewise stimulating the turnover of the mucopolysaccharide acids in the connective tissue, consequently preserving the functionality of the connective matrix.

Within the scope of the present invention the triterpenes of *Centella asiatica* can be utilised in the form of dry extracts or, preferably, in phytosomal form that is—as it has been mentioned—in a form complexed with phospholipids for improving the absorption thereof by the organism.

The extracts of fish cartilage, used in the scope of the invention, comprise as active principle, chondroitin sulphate constituted by a mixture of mucopolysaccharide acids, formed by a repetitive linear unit containing different sulphate groups. The basic units are constituted by N-acetylgalactosamine and glucuronic acid.

The use of anhydrous extract shark cartilage is particularly preferred.

Tests conducted by the applicant have made it possible to ascertain that the association of the active principles mentioned above performs an effective anti oxidant action acting to limit the cutaneous damage caused by free radicals, an anti collagagenasic and anti elastasic action directed at limiting the damage consequent upon the release of those metalloproteases involved in the photo exposure inflammatory cascade after photo exposure which is the source of those connective scars responsible in time for the cutaneous sinking identified as wrinkles, a procollagenogenetic action directed at reconstructing the pool of connective collagen destroyed by the protease released following photo exposure and an excellent tropism for the connective and cutaneous tissue.

In a preferred embodiment the basic composition according the invention comprises:

- 5-200 parts by weight of extract of *Centella asiatica*, preferably in phytosomal form;
- 10-300 parts by weight of extract of leucocyanadine, preferably in phytosomal form; and
- 50-1000 parts by weight of shark cartilage.

Commercially available standardised extracts can be utilised for the preparation of the composition.

In the case of compositions intended for subjects who are smokers, it is preferable that the composition contains, in association with the said active principles, also lycopene, which consists of a carotenoid acyclic lipophilic extract from the skin of tomato free from "provitamin A" type activity which has a powerful antioxidant activity. Lycopene can be typically utilised in quantities from 0.1 percent by weight to 1 percent by weight referred to 100 parts by weight in total of the basic mixture, constituted by the above mentioned components.

Particularly in the case of compositions intended for the treatment of wrinkles in menopausal women it is preferable that the composition contains—in association with the said active principles—soya isoflavones; for this purpose commercial extracts of soya isoflavones can be utilised, preferably in quantities from 20-60% by weight with reference to 100 parts by weight of the basic composition constituted by the extracts of *Centella asiatica*, leucocyanadine and fish (shark) cartilages.

Compositions for use on men, particularly for male subjects of an age greater then 40-45 years, further preferably comprise as active principle, the hormone dehydroepiandrosterone (DHEA) which can be introduced in to the formulation by means of the use of *Dioscorea* or steroid extract of YAM. The DHEA as such is preferably utilised in quantities from 5-40% —preferably from 5-20% by weight with reference to 100 parts by weight of the above mentioned basic mixture.

In a preferred embodiment the composition further includes dimeric flavones of *Ginkgo Biloba*, preferably in the form of phytosomes in which the active principles are complexed with phospholipids (particularly diastearoylphosphatidylcoline).

The said dimeric flavones are introduced into the composition by utilising extracts of *Ginkgo biloba* highly enriched in biflavonic component.

Five biflavones have been identified in particular in the biflavonic component of *Ginkgo biloba*, namely amentoflavone, bilobethine, isoginkgetine, ginkgetine and sciadopisine. Within the scope of the present invention the activity of the said dimeric flavones in the prevention and treatment of cutaneous ageing has been ascertained, presumably due to their micro vascular-kinetic properties. Their use is particularly useful for the treatment of cutaneous ageing in smokers.

The extracts of dimeric flavones are preferably used in the compositions in quantities from 2-30%; more preferably from 5-20% by weight referred to 100 parts by weight of the basic mixtures.

The composition can moreover include active principles chosen from eicosapentaenoic acid (EPA), docahexaenoic acid (DHA), γ-linolenic acid and their mixtures. Fish oil is a preferred source of eicosapentaenoic acid (EPA) and docahexaenoic acid (DHA) which, with reference to 100 parts by weight of the basic mixture, can be added in the amount of 5-80 percent by weight.

The γ-linolenic acid is preferably introduced into the formulation by the use of borage oil added in quantities from 30-80 percent by weight referred to 100 parts by weight of the basic mixture. Alternatively, or in combination with borage oil, the invention contemplates the use of oil of evening primrose (eonothera) in equal quantities.

Vitamins, particularly vitamin E, vitamin C and β-carotene can also be included in the compositions, as can micronutrients and mineral salts as solids, zinc and/or selenium.

The composition according to the invention is formulated in a form suitable for oral administration, in particular capsules of soft or hard gelatine shells, tablets, pills, elixirs, suspensions and syrups.

The forms of administration can include excipients and/or binders and/or pharmaceutically acceptable vehicles, in particular lecithin and mono and diglycerides of fatty acids.

By way of example, a typical formulation can be formulated according to the data shown in the following table where, for the components of the basic mixture and for the optional components there are indicated the minimum and maximum quantities preferred, expressed in parts by weight.

| Components Of Basic Mixture | A Parts By Weight (min) | % | B Parts By Weight (max) | % |
|---|---|---|---|---|
| Cartilage | 50 | | 1000 | |
| Leucocyanidine (extract) | 10 | | 300 | |
| *Centella asiatica* (extract) | 20 | | 200 | |
| | 80 | 100 | 1500 | 100 |

| Optional Components | C Parts By Weight (min) | C/A *100 | D Parts By Weight (min) | D/B *100 |
|---|---|---|---|---|
| Isoflavones (soya extract) | 48 | 60 | 600 | 40 |
| Dimeric flavones | 10 | 12.5 | 50 | 3.3 |
| Lycopene | 0.10 | 0.125 | 10 | 0.1667 |
| DHEA (as such) | 15 | 18.75 | 150 | 10 |
| Vitamin E | 10 | 12.50 | 200 | 13.33 |
| Zinc as ions | 5 | 6.25 | 15 | 1.0 |
| Borage oil or EPO (oenothera) | 50 | 62.50 | 1000 | 66.7 |
| Fish Oil | 50 | 62.50 | 750 | 50 |

In the above table the values shown, expressed in parts by weight, when expressed in mg correspond to minimum and maximum advised daily dosages.

The efficacy of the composition according to the invention has been determined by means of studies effected of female subjects free from cutaneous and/or systemic pathologies. Capsules have been utilised with cases of soft gelatine containing:

- extract of *Centella asiatica:* 20 mg/cps
- extract of leucocyanadine: 50 mg/cps
- shark cartilage: 250 mg/cps
- soya lecithin: 50 mg/cps
- fish oil: 120 mg/cps
- borage oil: 240 mg/cps
- Vitamin E: 15 mg/cps
- Zinc: 5 mg/cps.

The subjects took three capsules per day of the product under examination for ninety days and the results obtained were compared with the results of a corresponding number of subjects to when a placebo was administered.

Evaluation of the photo ageing was effected by measurement by the following biophysical parameters: cutaneous thickness by ultrasound at 20 MHz, biomechanical functions of the skin in particular elasticity, stretchability, viscoelasticity and micro circulation by Doppler laser velocimeter and evaluation of the depth of the wrinkles, performed by the technique of cutaneous replication with image analysis.

Whilst the subjects treated with placebo exhibited no significant changes, in the group treated with the active principles there was detected a significant increase in the microcirculatory values, cutaneous thickness and bio mechanical function of the skin both in terms of stretchability, viscoelasticity, and elasticity.

Moreover, analysis of the images of the skin replicas showed a reduction in the depth of the wrinkles with particular reference to the deepest wrinkles and to the undulations of the skin.

The compositions, moreover, have been found useful for reducing skin stretch marks and cutaneous relaxations.

The invention claimed is:

1. An oral composition based on natural extracts useful in the treatment of cutaneous aging, skin stretch marks and skin relaxations, the composition being in the form of a dosage unit for oral administration, the composition comprising:
    about 10-300 parts by weight leucocyanadines complexed with phospholipids of an extract of *Vitis vinifera*;
    about 5-200 parts by weight triterpenes complexed with phospholipids of an extract of *Centella asiatica*; and
    about 50-1000 parts by weight extract of fish cartilage.

2. A composition according to claim 1, further comprising one or more components selected from the group consisting of:
    from 48-600 parts by weight of soya extract containing isoflavones;
    from 0.1-10 parts by weight of lycopene;
    from 15-150 parts by weight of dehydroepiandrosterone;
    from 50-1000 parts by weight of borage oil or oil of evening primrose;
    from 10-50 parts by weight of extracts of dimeric flavones; and
    from 50-750 parts by weight of fish oil.

3. A composition according to claim 1 further comprising from 0.1-1 percent by weight of lycopene based on 100 parts by weight of the composition.

4. A composition according to claim 1, for the treatment of cutaneous aging in menopausal female subjects, the composition further comprising:
    extract of soya containing isoflavones in a quantity from 20-60% by weight based on 100 parts by weight of the composition.

5. A composition according to claim 1, for the treatment of cutaneous aging phenomena in male subjects, further comprising:
    from 5-40 percent by weight of dehydroepiandrosterone from extract of *Dioscorea* based on 100 parts by weight of the composition.

6. A composition according to claim 1, further comprising at least one component selected from the group consisting of fish oil, borage oil, oil of evening primrose (Oenathera), vitamins, micro nutrients and salts of zinc.

7. A composition according to claim 1, wherein the extract of fish cartilage is an extract of shark cartilage.

8. A composition according to claim 1, further comprising chondroitin sulfate.

9. A composition according to claim 8, further comprising a component selected from the group consisting of madecassic acid, asiatic acid, asiaticoside, and mixtures thereof.

10. A composition according to claim 9, further comprising procyanidolic oligomers of *Vitis vinifera*.

11. The composition of claim 1, wherein the composition includes at least one component selected from the group consisting of an excipient, binders and pharmaceutically acceptable vehicles.

12. The composition of claim 1, wherein said triterpenes are included in an amount effective to accelerate the uptake and metabolism of lysine and proline.

13. An oral composition in the form of a dosage unit for oral administration and being based on natural extracts useful in the treatment of cutaneous aging and wrinkles, wherein the composition comprises, as active components in combination, procyanidolic oligomers of *Vitis vinifera*, chondroitin sulphate, and at least one component selected from the group consisting of madecassic acid, asiatic acid and asiaticoside and a mixture thereof.

14. A composition according to claim 13, further comprising at least one component selected from the group consisting of lycopene, isoflavones of soya and dehydroepiandosterone (DHEA).

15. A composition according to claim 13, further comprising triterpenes in the form of an extract of *Centella asiatica* and an extract of fish cartilage.

16. A method for treating cutaneous aging, skin stretch marks and skin relaxations, comprising orally administering to a patient in need thereof an effective amount of an oral composition comprising:
    leucocyanadines complexed with phospholipids of an extract of *Vitis vinifera*;
    triterpenes complexed with phospholipids of an extract of *Centella asiatica*; and
    extract of fish cartilage.

17. The method of claim 16, wherein the composition further comprises:
    from 5-200 parts by weight of the extract *Centella asiatica*;
    from 10-300 parts by weight of the extract of *Vitis vinifera* containing the leucocyanidin; and
    from 50-1000 parts by weight of fish cartilage.

18. The method of claim 17, wherein the composition further comprises at least one component selected from the group consisting of:
    from 48-600 parts by weight of soya extract containing isoflavones;
    from 0.1-10 parts by weight of lycopene;
    from 15-150 parts by weight of dehydroepiandosterone;
    from 50-1000 parts by weight of borage oil or oil of evening primrose;
    from 10-50 parts by weight of extracts of dimeric flavones; and
    from 50-750 parts by weight of fish oil.

19. The method of claim 16, wherein the composition further comprises:
    from 0.1-1 percent by weight of lycopene based on 100 parts by weight of the composition.

20. The method of claim 16, wherein the patient is a menopausal female, and wherein the composition further comprises:
    extract of soya containing isoflavones in a quantity from 20-60% by weight based on 100 parts by weight of the composition.

21. The method of claim 16, wherein the patient is a male subject, and wherein the composition further comprises:
    from 5-40 percent by weight of dehydroepiandosterone from extract of *Dioscorea* based on 100 parts by weight of the composition.

22. The method of claim 16, wherein the composition further comprises at least one component selected from the group consisting of fish oil, borage oil, oil of evening primrose (*Oenathera*), vitamins, micro nutrients and salts of zinc.

23. The method of claim 16, wherein the extract of fish cartilage is an extract of shark cartilage.

24. A method for treating cutaneous aging and wrinkles, comprising orally administering to a subject in need thereof an effective amount of an oral composition comprising as active components, procyanidolic oligomers of *Vitis vinifera*, chondroitin sulphate, and at least one component selected from the group consisting of madecassic acid, asiatic acid, asiaticoside and a mixture thereof.

25. The method of claim 24, wherein said composition comprises at least one component selected from the group consisting of lycopene, isoflavones of soya and dehydroepiandosterone (DHEA).

26. The method according to claim 24, wherein said composition further comprises triterpenes in the form of an extract of *Centella asiatica* and an extract of fish cartilage.

* * * * *